(12) United States Patent
Smajlovic

(10) Patent No.: US 9,005,979 B2
(45) Date of Patent: Apr. 14, 2015

(54) METHOD FOR DETERMINING ORIGIN OF ALCOHOL OR SUGAR CONTAINING PRODUCTS

(76) Inventor: Ivan Smajlovic, Becej (RS)

( * ) Notice: Subject to any disclaimer, the term of this patent is extended or adjusted under 35 U.S.C. 154(b) by 582 days.

(21) Appl. No.: 12/972,472

(22) Filed: Dec. 18, 2010

(65) Prior Publication Data
US 2011/0136097 A1 Jun. 9, 2011

Related U.S. Application Data

(63) Continuation-in-part of application No. 12/989,414, filed as application No. PCT/RS2008/000022 on Jun. 19, 2008, now abandoned.

(30) Foreign Application Priority Data

May 15, 2008 (RS) .................................. P-2008/0208

(51) Int. Cl.
| | | |
|---|---|---|
| C12Q 1/00 | (2006.01) | |
| G01N 33/53 | (2006.01) | |
| G01N 33/14 | (2006.01) | |
| G01N 33/02 | (2006.01) | |

(52) U.S. Cl.
CPC .......... *G01N 33/5308* (2013.01); *G01N 33/146* (2013.01); *G01N 2560/00* (2013.01); *Y10S 250/91* (2013.01)

(58) Field of Classification Search
USPC ......... 250/282, 910, 283; 702/24; 436/24, 20; 435/4
See application file for complete search history.

(56) References Cited

U.S. PATENT DOCUMENTS

| | | | |
|---|---|---|---|
| 3,283,027 A | 11/1966 | Lundeen | |
| 5,424,539 A | 6/1995 | Brand | |
| 2008/0312485 A1* | 12/2008 | Takai et al. | .................. 585/640 |

FOREIGN PATENT DOCUMENTS

| | | |
|---|---|---|
| EP | 1953129 A1 | 8/2008 |
| WO | WO2007055361 A1 | 5/2007 |

OTHER PUBLICATIONS

Dunbar et al. Measurement of the H/H Ratios of the Carbon Bound Hydrogen Atoms in Sugars(1984). Analytical Chemistry. 853-857.*
Kelly et al. Emerging Techniques in Vegetabe Oil Analysis Using Stable Isotope Ratio Mass Spectrometry(2002). Grasa y Aceites.34-44.*

(Continued)

*Primary Examiner* — Rebecca M Fritchman
(74) *Attorney, Agent, or Firm* — Erickson Law Group, PC

(57) ABSTRACT

A method for determining origins of food products, and more specifically for determining geographic and/or biological origin of food products containing alcohols or sugars includes preparing an alcohol sample from a product in question, removing exchangeable hydrogen/deuterium atoms from alcohol molecules of the sample, determining the isotopic composition of non-exchangeable hydrogen/deuterium atoms from sample alcohol, and analyzing results for adulteration or determination of product origin. In addition, alcohol $\delta^{13}C$ and $\delta^{18}O$ isotopic values, along with $\delta^{18}O$ isotopic value of the product water are used for the analysis. Products containing sugar are also subjected to tightly controlled fermentation.

23 Claims, 10 Drawing Sheets

(56) References Cited

OTHER PUBLICATIONS

Calderone, Isotopic analysis of ethanol: study of O-18/O-16 measurement using a high-temperature pyrolysis system coupled to an isotope ratio mass spectrometer, Rapid Comunication in Mass Spectrometry, vol. 20, 2006, pp. 937-940, XP002512894, ISSN: 0951-4198, Published online in Wiley InterScience www.interscience.wiley.com.

Smith, A rapid method of qualitative and quantitative analysis of products from pyrolysis, Analyst, Royal Society of Chemistry UK, vol. 86, Jul. 1961, pp. 480-483, XP002512893, ISSN:0003-2654, UK.

Ishida-Fujii, Botanical and Geographical Origin Identification of Industrial Ethanol by Stable Isotope Analyses of C, H, and O; Biosci, Biotechnol. Biochem., Japan Society for Bioscience, Biotechnology and Agrochemistry, 69 (11), pp. 2193-2199, Aug. 17, 2005, Japan.

* cited by examiner

**Authenticity of wines and fruit brandies
NEW APPROACH**

US 9,005,979 B2

METHOD FOR DETERMINING ORIGIN OF ALCOHOL OR SUGAR CONTAINING PRODUCTS

RELATED APPLICATIONS

The present application is continuation-in-part of application Ser. No. 12/989,414 filed on Oct. 23, 2010, which claims the benefit of priority of International Patent Application No. PCT/RS2008/000022 filed on Jun. 19, 2008, which claims priority of Serbian Patent Application No. P-2008/0208 filed on May 15, 2008. The entire texts of the priority applications are incorporated herein by reference in their entireties.

TECHNICAL FIELD

This invention relates generally to a method for determining origins of food products, and more specifically for determining geographic and/or biological origin of food products containing alcohols or sugars.

BACKGROUND

There is a great need for an inexpensive method for detecting adulteration and determining exact origin of products containing alcohols or sugars. For example, geographic and biological origins of wine products are important factors for determining their value. Consequently, consumers are concerned about the possibility of adulteration, especially regarding more expensive wines. Adulteration may be perpetrated during the production of the wine by adding undesired grape material or even sugars from other sources such as sugar beets. Furthermore, wine can be adulterated by diluting the final product with cheaper, lower quality, wines.

To address this problem, in 1990 the European wine industry adopted a method for detecting wine adulteration using Site-Specific Natural Isotope Fractionation-Nuclear Magnetic Resonance (SNIF-NMR). The SNIF-NMR measures relative deuterium concentration and specific deuterium-site locations in wine ethanol molecules, primarily to detect adulteration with beet sugar. The SNIF-NMR method, however, requires expensive instruments and the procedure is relatively imprecise.

For example, for measurements taken with the standard NMR method, as shown in FIG. 1, the repeatability for $^2$H-NMR is 0.3 ppm and the effect of enrichment is 0.1 ppm for 0.1% vol. Using 2-fold standard deviation as criteria for repeatability (0.6 ppm), the detection threshold is calculated to approximately 0.6% vol. More specifically, the results for SNIF-NMR method suggest that measured difference between grape and beet sugar is only approx. 3 ppm vs. TMU for methyl-site isotope composition. Since these values are close and have a relatively wide range, e.g., 99 to 106 ppm vs. TMU for grape, and 87.5 to 97.5 ppm vs. TMU for beet sugar, it can be challenging, if not impossible, to determine botanical origin without comparing to results from a database containing data for unadulterated wines. In other words, because of the low sensitivity of the SNIF-NMR method and because the measurement results alone cannot be used to reliably detect adulteration by sugars for fermentation from non-grape sources, it is necessary to create a database for storing results from wine samples to be used for comparison.

On the other hand, the results from tests conducted according to the present invention suggest that the effect of enrichment is about 7% for each 10% of the enrichment for absolute isolated ethanol from wine ethanol with a standard deviation of 1.34%, and the effect of enrichment is 0.7% for each % vol. of ethanol from chaptalization (calculated for wine with 10% vol. alcohol). If a 2-fold standard deviation is used as a criteria for repeatability (2.68%), it should be possible to detect values as low as approximately 0.38% vol. for wine ethanol.

Another method that is widely used for authentication of food products is based on measuring the oxygen stable isotope ratio. This method, however, has limited applicability detecting only sweetening or watering of liquid food products, but not the source of the original material. This analysis generally includes extracting the oxygen and its stable isotopes, and measuring the $^{18}$O/$^{16}$O isotope ratio. The extraction of oxygen usually includes a carbon-dioxide molecular equilibration or pyrolysis.

Thus, there is a need for a method for determining the origin of alcohol or sugar containing products that is accurate, portable, and inexpensive.

DETAILED DESCRIPTION

Figure 1:
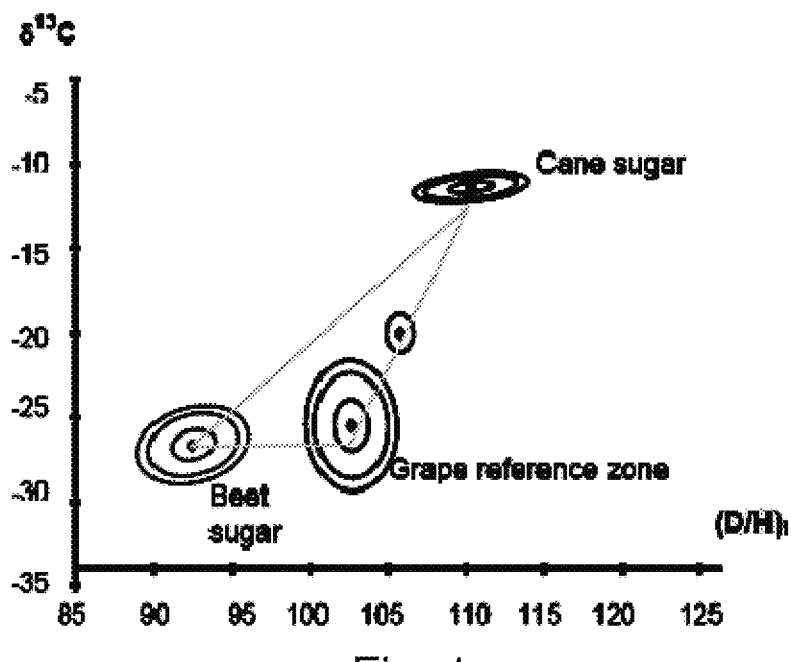
FIG. 1 depicts the correlation of $\delta^{13}$C and the relative ration of hydrogen stable isotopes $^2$H/$^1$H (D/H) from methyl sites of ethanol measured with SNIF-NMR method.

In nature, organic elements, such as carbon (C), hydrogen (H), and oxygen (O) are mixtures of two or more stable isotopes and the concentration of each isotope in organic molecules is influenced by their origin. Relative isotope concentration is a function of the isotope content of the starting material, various physical processes, chemical reactions, and biochemical pathways engaged in the creation of a given organic molecule. Thus, the origin of organic materials used in food and beverage preparation can often be determined by measuring relative isotopic ratios $^2H/^1H$ (D/H), $^{18}O/^{16}O$, $^{13}C/^{12}C$ of the final product.

For example, the deuterium D, which occurs naturally as a small fraction of hydrogen isotopes, is not distributed uniformly throughout the globe. In plants, the deuterium distribution in a sugar molecule varies as a function of the environmental conditions and specific photosynthetic pathways used in its synthesis. Thus, sugars from different plants have specific isotope ratios, which are also influenced by climate conditions and the area of origin. In conclusion, the isotope ratio is reflected in the final product originating from certain areas, which can be used as its isotopic "fingerprint."

When sugars are fermented, the isotope distribution of the resulting alcohols parallels the distribution and relative concentration of deuterium in the sugar molecule, thus allowing the determination of the alcohols' geographic and biologic origins. The deuterium/hydrogen (D/H) ratios measured at the methyl and methylene sites of ethanol differ significantly according to the origin of the sugar from which the alcohol is produced. More specifically, comparison of methyl D/H ratios and ratios of methyl and methylene signals in deuterium spectra enables discrimination between original and adulterated products, and between unadulterated products having different geographical origins.

An isotopic content (δD) of a sample can be expressed relative to the international standard V-SMOW (Vienna Standard Mean Ocean Water) in parts per thousand:

$$\delta D(\%) = [(R-Rs)/Rs] \times 1000 = (R/Rs - 1) \times 1000,$$

where R represents the D/H ratio of the sample, Rs represents the eD/H ratio of the international standard V-SMOW (Vienna Standard Mean Ocean Water), and Rs=155.76±0.005 ppm.

Alcohol molecules comprise exchangeable and non-exchangeable hydrogen atoms and stable isotopes. The exchangeability attribute refers to the ability of atoms in alcohol molecules to establish bonds with surrounding water molecules or with molecules of other solvents, which causes atoms in alcohol molecules to be "exchanged" with atoms from the surrounding solvent. Hydrogen or deuterium atoms that are bonded to carbon atoms, i.e., to a methylene site, are non-exchangeable because they do not establish bonds with water molecules. On the other hand, hydrogen or deuterium atoms that are bonded to oxygen atoms in hydroxyl groups are exchangeable. As a consequence, ethanol is always in constant dynamic isotope equilibrium with its environment because of its hydroscopic nature and characteristic to form hydrogen bonds with its surrounding media, mostly due to easily exchangeable hydrogen (or deuterium) atoms in the hydroxyl group. Adding water with a different isotopic profile will disturb the existing dynamic isotope equilibrium of the mixture, causing hydrogen isotope shift and producing new isotope balance.

In this application, examples and explanations often include ethanol. However, the present invention is not limited to ethanol, and applies to other alcohols as well. The descriptions of chemical reactions involving ethanol are intended for illustration purposes only, and are not limited to ethanol, including the alcohol products formed in described chemical reactions. For example, the process of dehydration of an alcohol results in production of its respective olefin (alkene), e.g., propene from propanol. Similarly, the process of dehydrogenation of an alcohol results in production of related aldehydes and ketons.

Figure 2:
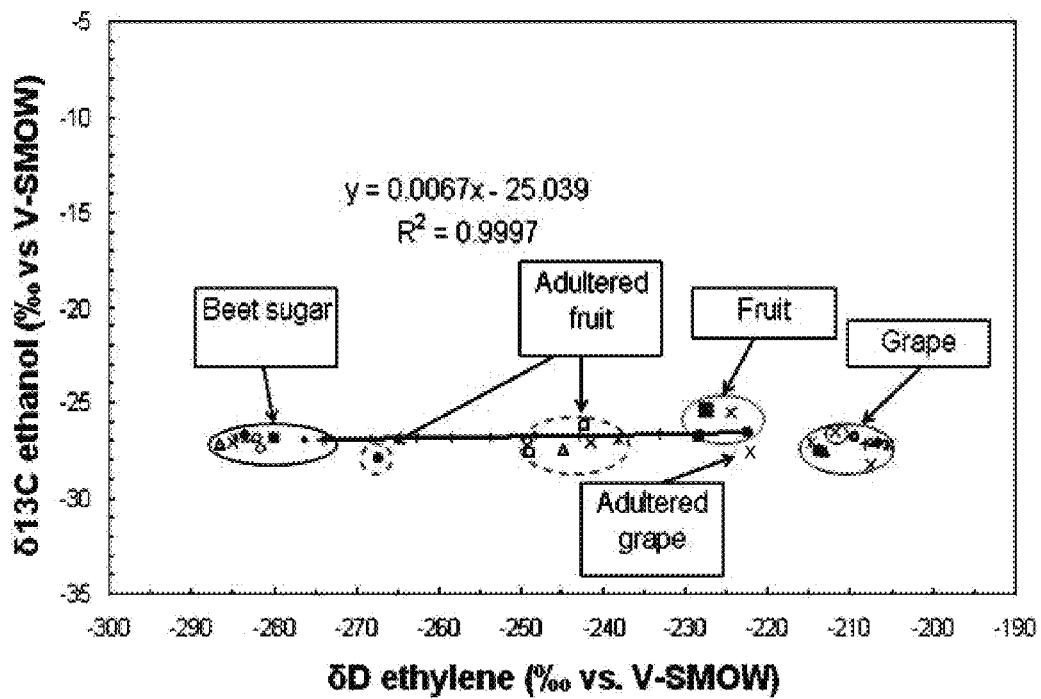
FIG. 2 depicts the correlation of $\delta^{13}$C and $\delta$D values in ethanol from grape wines, fruit brandies and beet sugar measured using the standard IRMS methods.
Figure 3:
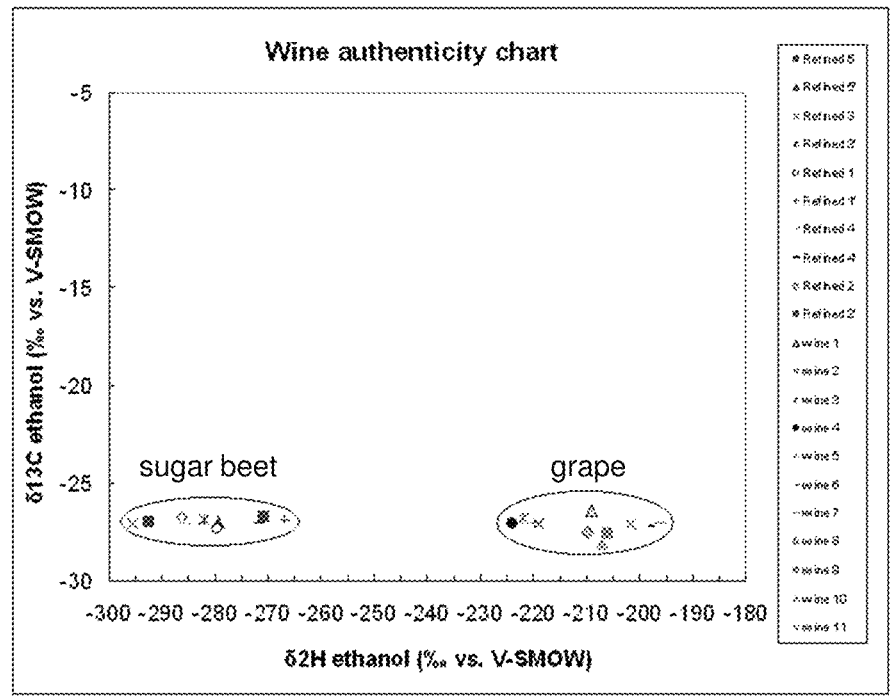
FIG. 3 depicts the correlation of $\delta^{13}$C and $\delta$D values in ethanol which originates from beet sugar and grape measured using the standard IRMS methods.

Furthermore, during the distillation of an ethanol-water mixture, a phenomenon called "isotopic fractionation" occurs. Distillation disturbs the dynamic equilibrium of ethanol and the surrounding water in liquid phase, thus changing the isotope profile of the distilled ethanol. Because of this effect, the δD values for the ethanol samples often vary, and commercially available instruments based on continuous-flow pyrolysis and Isotope Ratio Mass Spectrometer (IRMS) are not used for determining botanical origins of ethanols. As shown in FIGS. 2 and 3, measured ethanol δD and $\delta^{13}C$ values are scattered, overlapping, and the measured values are generally non-repeatable.

Figure 4:
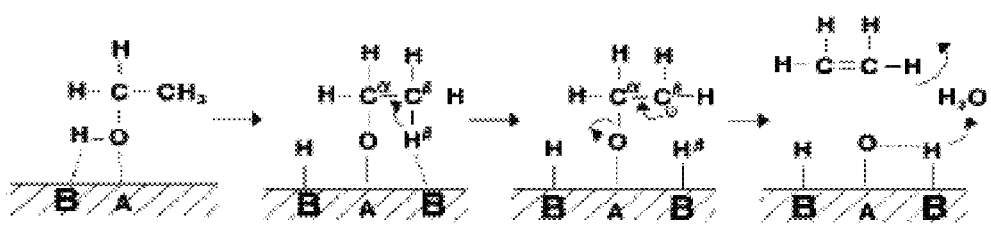
FIG. 4 depicts a chemical mechanism of dehydration of ethanol on the surface of the catalyst.

However, non-exchangeable hydrogen and deuterium atoms that are bonded to the carbon atoms of alcohol can provide important information about the alcohol origin. According to one embodiment, exchangeable hydrogen and deuterium atoms are removed by a process of intra-molecular dehydration of alcohol, preferably over a solid dehydration catalyst, such as alumina $Al_2O_3$ or similar materials. The dehydration process is preferably based on an E2 elimination mechanism that involves only one step with no intermediates and resulting in the formation of olefins and water as reaction products. FIG. 4 depicts the mechanism of the ethanol molecule dehydration during the interaction with the catalyst surface. Both acetic (A) and basic (B) sites of the catalyst react with alcohol molecules without the formation of ionic intermediates. According to another embodiment, exchangeable hydrogen and deuterium atoms are removed by a process of dehydrogenation of alcohol, preferably over a dehydrogenation catalyst.

Figure 5:
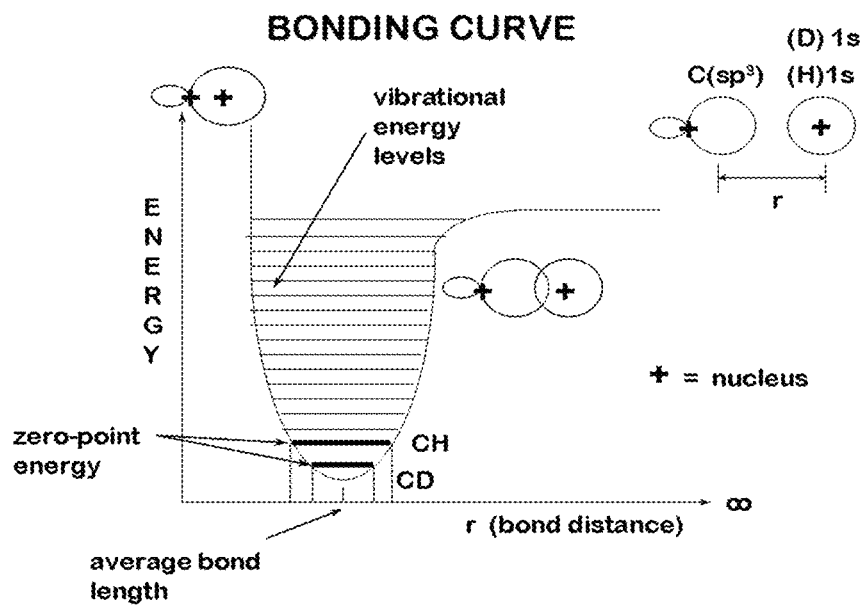
FIG. 5 depicts the energy bonding curve for C-D and C—H bonds.

As shown in FIG. 5, the bond-dissociation energy required for breaking carbon-deuterium (C-D) bonds is generally greater than the energy required for breaking carbon-hydrogen (C—H) bonds. The deuterium atoms are heavier than hydrogen atoms and C-D bonds vibrate slower and over a shorter distance compared to the C—H bond. Consequently, this Kinetic Isotope Effect (KIE) suggests that C—H bonds have approximately ten times greater susceptibility toward chemical reactions than C-D bonds. As a consequence, during the dehydration of alcohols, hydroxyl groups and hydrogen atoms from the methyl sites of alcohol molecules are separated from alcohol molecules, but the deuterium atoms stay bonded to β-carbon atoms. The chemical reaction can be represented as follows:

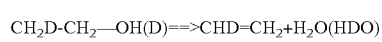

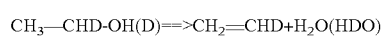

Preferably, the reaction includes heating an alcohol sample to around or above 350° C., and passing the alcohol fumes (vapors) over a catalyst such as $Al_2O_3$.

Figure 6:
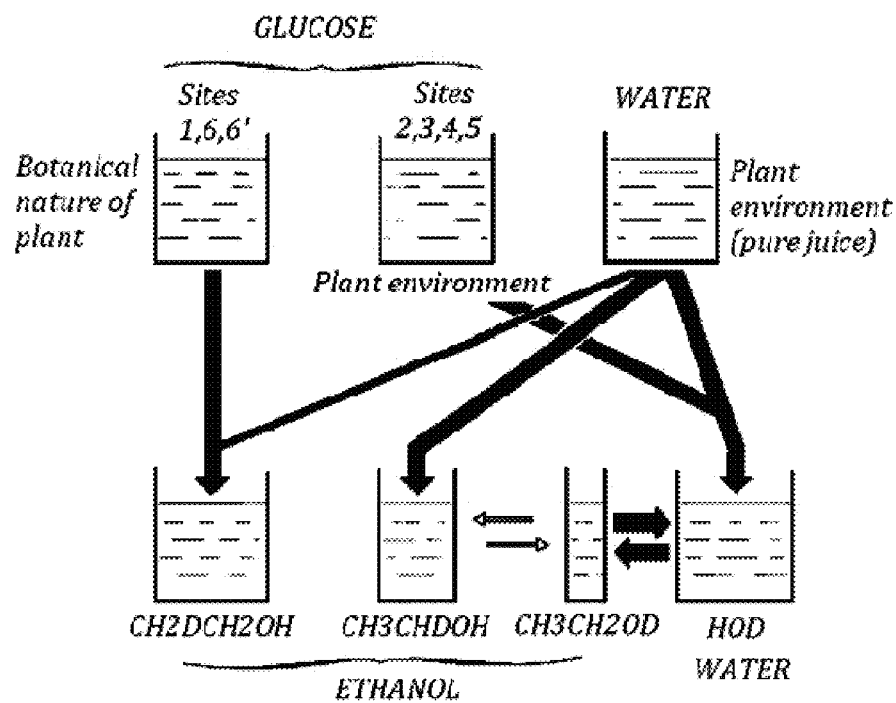
FIG. 6 depicts the redistribution of deuterium atoms during alcohol fermentation.

FIG. 6 shows a redistribution of deuterium atoms originating from glucose and water into ethanol molecules during alcohol fermentation. The hydrogen and deuterium atoms that are initially bonded at 1, 6, 6' sites of glucose molecule are mostly redistributed to methyl sites of ethanol molecules. As a consequence, the relative ratio of hydrogen stable isotopes at the methyl sites of ethanol molecules is indicative of the origin of sugar that was used in fermentation. Conversely, hydroxyl groups of grape sugar are comprised of hydrogen and deuterium atoms that are in constant dynamic equilibrium with surrounding water in the grape must and over 80% of this hydrogen is equilibrated with water during alcoholic fermentation. During the fermentation, these hydroxyl hydrogen and deuterium atoms are mostly redistributed to the methylene sites of ethanol molecules. More specifically, the exchange of hydroxyl hydrogen with the surrounding medium, which will later be redistributed to the methylene site of the ethanol, occurs at the triose phosphate level in the sequence of triose phosphate isomerase-aldolase-glyceraldehyde diphosphate dehydrogenase during alcoholic fermentation. These three steps are listed in probable order of decreasing rate, and the final step occurs under conditions in which the decarboxylation of pyruvate and the reduction of acetaldehyde generally determine the isotope composition. This means that the relative ratio of hydrogen stable isotopes at the methylene site of ethanol will retain information about the climatology of the site of production of the grapes, such as type of rain-water and weather conditions, and, to a lesser extent, sugar concentration in the original grape must.

In conclusion, non-exchangeable hydrogen stable isotopes in grape ethanol and their relative ratio $\delta D$ are mostly influenced by the following factors: 1) the climatic conditions and geographical location of the vineyards, 2) the grape is a naturally closed biochemical system with all its organic compounds in a closed and constant dynamic equilibrium, 3) the hydrogen atoms of grape water are equilibrated with hydrogen atoms from hydroxyl sites of sugar, and 4) the enzymatic peculiarities associated with specific kinetic and thermodynamic isotope effects at various steps of metabolism during alcohol fermentation. Therefore, if the fermentation medium is genuine, the $\delta D$ of non-exchangeable hydrogen stable isotopes in ethanol produced in such an environment would be specific and constant, and the measured results would be repeatable and within a narrow range. According to one embodiment of the present invention, exchangeable hydrogen and deuterium atoms bonded to oxygen atoms in hydroxyl groups are removed, preferably through the process of alcohol dehydration. The process of alcohol dehydration produces olefins, such as ethylene which is produced from ethanol, and the $\delta D$ value of olefins is measured.

Figure 7:
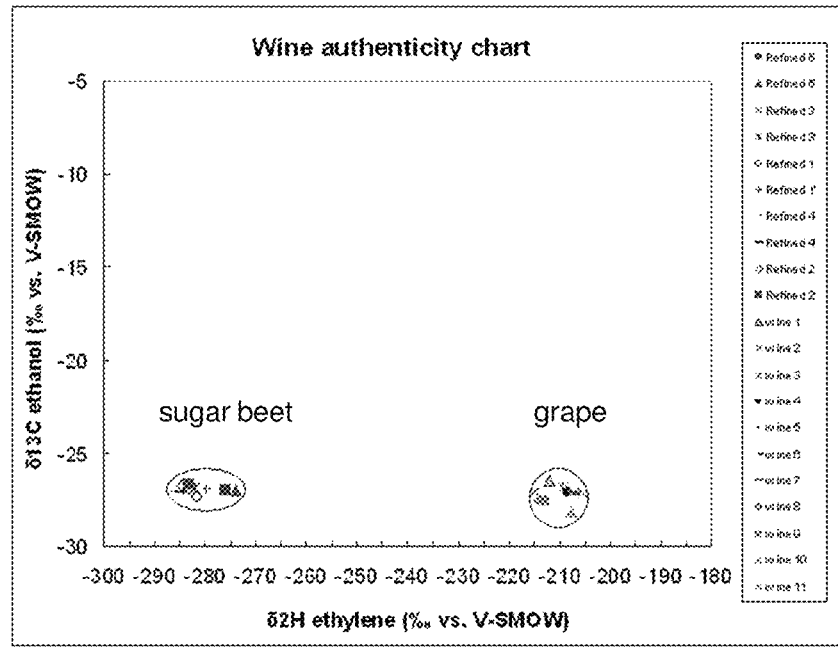
FIG. 7 depicts the correlation of ethanol $\delta^{13}$C values and ethylene $\delta$D values ($\delta$D values of non-exchangeable hydrogen stable isotopes of ethanol) for sugar beet and grape ethanol measured in accordance with various embodiments of the invention.
Figure 8:
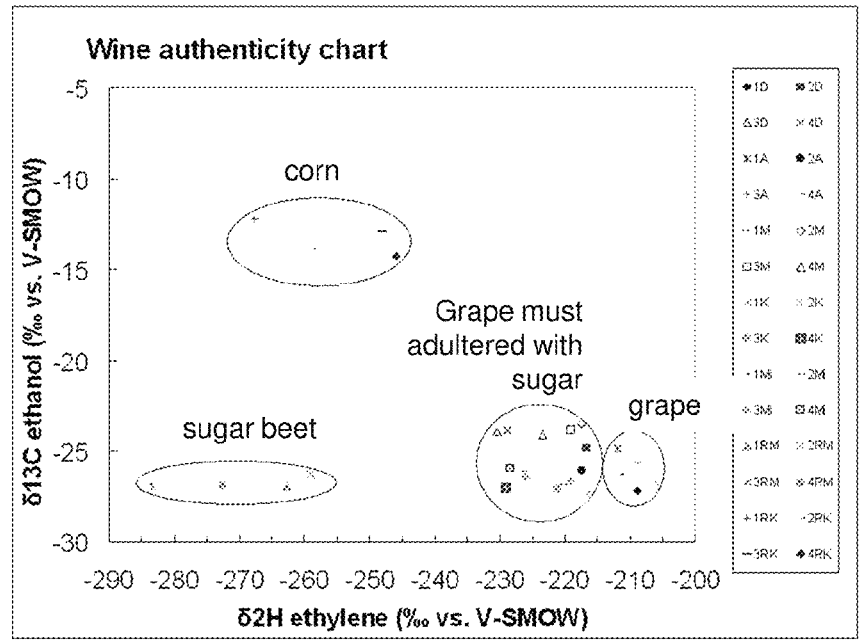
FIG. 8 depicts the correlation of ethanol $\delta^{13}$C values and ethylene $\delta$D values ($\delta$D values of non-exchangeable hydrogen stable isotopes of ethanol) for authentic ethanol from different sources (grape, beet sugar, corn) and adultered grape ethanol (grape must adultered with the addition of sugar) measured in accordance with various embodiments of the invention.
Figure 9:
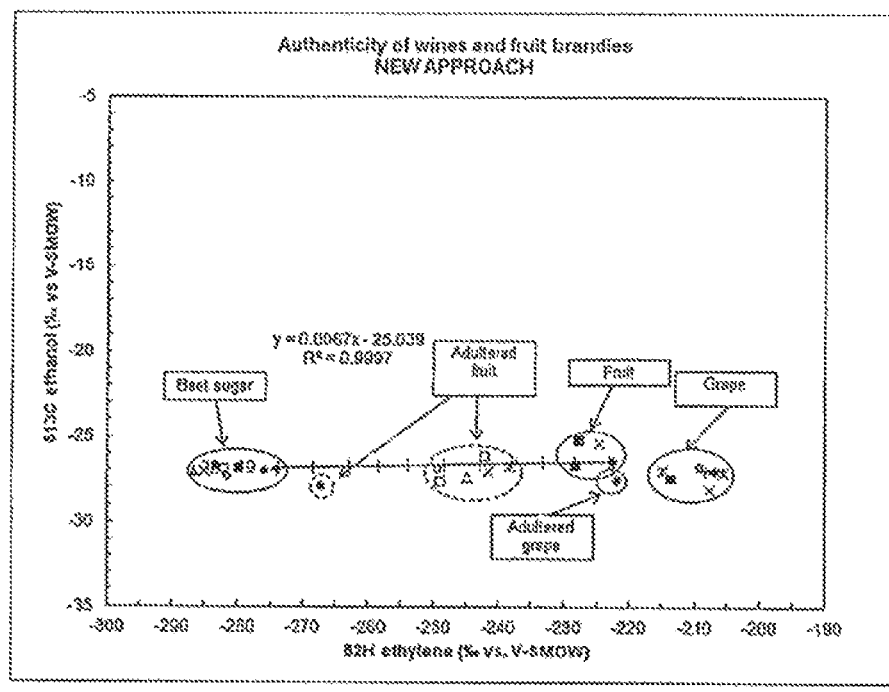
FIG. 9 depicts the correlation of ethanol $\delta^{13}$C and ethylene $\delta$D values ($\delta$D values of non-exchangeable hydrogen stable isotopes of ethanol) for grape ethanol, fruit ethanol, sugar beet ethanol and for adultered fruit and grape ethanol measured in accordance with various embodiments of the invention.
Figure 10:
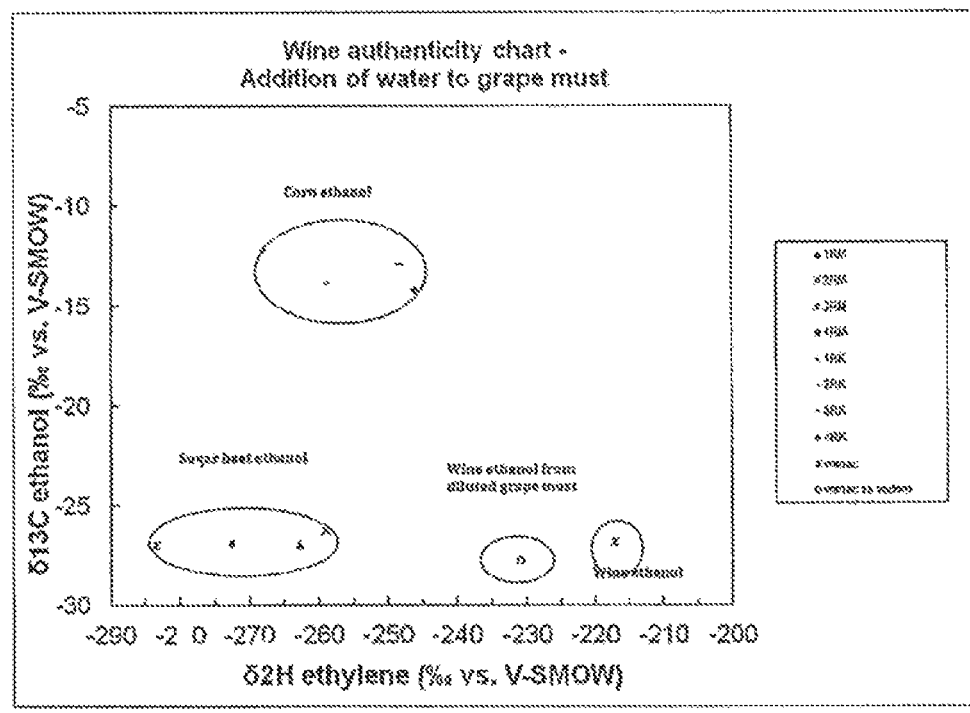
FIG. 10 depicts the correlation of ethanol $\delta^{13}$C and ethylene $\delta$D values ($\delta$D values of non-exchangeable hydrogen stable isotopes of ethanol) for authentic wine ethanol, ethanol from wine made from diluted grape must, sugar beet ethanol, and corn ethanol measured in accordance with various embodiments of the invention.

As shown in FIG. 7, $\delta D$ values of ethylene measured according to the present invention for sugar beet ethanol and for grape ethanol are grouped in separate, small, and concentrated clusters. Thus, it is also possible to differentiate alcohols from different sources in addition to detecting adulteration. As shown in FIG. 8, any addition of sugars from other sources, such as sugar beets or corn, results in much more negative $\delta D$ values in comparison to ethanol originated from pure grape must.

Furthermore, by comparing ethylene $\delta D$ values obtained using the ethylene method and $\delta^{18}O$ isotopic values of the originating wine, it can be determined if water or sugar was added to the grape must of an unknown wine. More specifically, if sugar was added, ethylene $\delta D$ values would be more negative while wine $\delta^{18}O$ would remain unchanged. If water was added to the grape must prior to alcoholic fermentation, the ethylene $\delta D$ value and wine $\delta^{18}O$ value would be more negative. If water was added after fermentation (dilution of wine) then the ethylene $\delta D$ value would be more positive, unchanged, and inside the reference zone for authentic grape ethanol, but the $\delta^{18}O$ value would be more negative. Thus, this method can be used to determine exactly what illegal practice was committed during the production of wine.

Furthermore, the relative ratio of non-exchangeable hydrogen stable isotopes in an ethanol sample (ethylene $\delta D$ values) also depends on the botanical origin of the ethanol. As shown in FIG. 8, alcohol refined from sugar beets or corn have generally more negative natural ethylene $\delta D$ values in comparison to ethanol produced from grapes, which is due to the different physiology of these plants. Also, ethylene $\delta D$ values of sugar beets or corn generally are much more diverse than that of grape ethanol. Measurements of sugar beets and corn ethanol generally form larger clusters with greater deviation limits in comparison to grape ethanol. This phenomenon is mostly the consequence of production procedures. For example, refined ethanol from sugar beets is produced by the fermentation of diluted molasses, a viscous byproduct of processing sugar beets into sugar. The quality of molasses depends on the maturity of sugar beets, the amount of extracted sugar, and the method of extraction. Molasses is concentrated by evaporation into dry matter with concentration levels between 70-80%. Since molasses is mainly made up of dry matter it has to be diluted with water before fermentation. As a consequence, during the production of ethanol from sugar beets, two processes influence the dynamic equilibrium between hydrogen atoms from hydroxyl groups of molasses sugar and the surrounding medium: 1) the concentration of molasses and, 2) the dilution of molasses prior to alcoholic fermentation. Since different local surface waters with different isotopic profiles are used for the dilution of molasses, the relative ratio of hydrogen stable isotopes at the methylene site of ethanol will vary as well. Thus ethylene $\delta D$ values for sugar beets ethanol will have more diverse values because of the influence of the methylene D/H relative ratio on the overall D/H relative ratio in the ethylene. The same principle applies to ethanol from corn and sugar cane.

It is well known that local surface waters generally have more negative $\delta D$ values in comparison to water found in plants, i.e., surface waters have lower deuterium content, and hydrogen is more easily consumed than deuterium by coenzymes in biochemical conversions during alcoholic fermentation. As a consequence, ethanol originating from industrial plants like sugar beets, sugar cane, or corn has different, generally lower, concentrations of non-exchangeable deuterium atoms bonded to carbon atoms of ethanol.

Various embodiments of the present invention can also be used for determining the origin of food products containing sugar, such as fruit products, juices, and in the soft-drink syrup industry. For example, soft-drink syrup producers, such as the Coca-Cola Company, produce and ship soft-drink concentrates to licensed bottlers throughout the world. To ensure that the juice or syrup originate from a particular production plant or a production batch, a product sample must be prepared under strictly controlled conditions, its isotope concentration is measured, and the measured results are compared with the reference results obtained from the original product. The preparation of the sample includes adjusting the isotopic profile of the sample to a pre-determined value, which is preferably done by adding water with a surplus concentration of the hydrogen isotopes that are lacking in the sample. Adjusting the isotopic profile of a sample to a pre-determined value will offset the potential influence of hydroxyl hydrogen on the D/H relative ratio on the methylene sites of fermented alcohol. The sample with the adjusted isotopic profile is then subjected to controlled alcohol fermentation. An alcohol sample is extracted and the isotopic composition of the non-exchangeable hydrogen in the alcohol sample is measured. Measuring may also include the removal of exchangeable hydrogen and deuterium atoms bonded to oxygen atoms in hydroxyl groups, preferably through the process of alcohol dehydration. The measured isotopic value is compared with the known isotopic value of the original product. Since the original product is also measured after being adjusted to the same pre-determined isotopic profile, the difference between measured values from the original and suspected products would indicate whether the product originated from the claimed production plant or production batch.

Preferably, all production batches would be tested according to the present invention, and the measured values, along with the other production parameters such as ingredients and their sources, would be recorded. Thus, the origin of a questionable sugar-containing product, such as soft-drink syrup or juice, could be easily traced to a particular production plant and even individual production batch.

An embodiment of the present invention could be used for detecting the adulteration of wine, such as chaptalization and watering. The watering of grape must prior to alcoholic fermentation can be detected from ethylene $\delta D$ values that are out of the referent zone for grape, or that at least differ from the ethylene $\delta D$ values of an unadulterated wine. If beet sugar is added then the ethylene $\delta D$ value would be more negative, because the methyl deuterium ratio would be changed and then the overall deuterium ratio of ethylene would be changed. If water is added, then the ethylene value would be more positive or negative in accordance with the isotopic profile of the added water. Furthermore, from $\delta^{18}O$ isotope values of water molecules in wine along with ethylene $\delta D$ values of wine ethanol, it is possible to determine whether water or sugar is added during the production. A similar principle is applicable for determining the origin of food products containing fermentable sugars, such as juices or soft-drink syrups. For such products, however, in order to retrieve valid ethylene $\delta D$ values of ethanol, they should be subjected to fermentation under tightly controlled conditions, including adjusting the isotopic profile of the product to a pre-determined value prior to fermentation.

Methods for measuring $\delta^{18}O$ in solvents, e.g., water from wine, are well known in the art, such as the GasBench IRMS instrumental technique. According to this well known technique, a wine sample is equilibrated with $CO_2$ gas and the equilibrated $CO_2$ is introduced along with a helium carrier gas into the IRMS where the oxygen isotopic composition of $CO_2$ is measured.

According to another embodiment of the invention, since ethanol carbon atoms and oxygen atoms bonded to the methylene site of ethanol are non-exchangeable, $\delta^{18}O$ and $\delta^{13}C$ values of an ethanol sample, along with $\delta D$ values of the ethylene produced from the same ethanol sample, can be used for determining botanical and geographical origin of the product. The isotopic composition of oxygen and carbon in ethanol parallels those in sugars from which the sample ethanol is produced through the process of fermentation. The sugars are produced during the process of photosynthesis, which is specific to different botanical species, from plant water and carbon-dioxide, both of which are specific to particular geographical locations. As a consequence, an adulterated sugar and/or ethanol product will have at least one of the following three values: ethylene $\delta D$, ethanol $\delta^{13}C$, and ethanol $\delta^{18}O$ different from the unadulterated product sample, since it is impossible to adjust all three values to match those of an unadulterated product.

Methods for determining ethanol $\delta^{18}O$ value are also well known in the art. For example, $\delta^{18}O$ in wine ethanol can be measured using a TC/EA-IRMS (thermal conversion/elemental analyzer-Isotope Ratio Mass Spectrometer). The method includes pyrolysis of an ethanol sample at high temperatures (around 1400 degrees Celsius) in a helium stream to produce elemental Hydrogen and Carbon-monoxide gases. These gases are separated over a molecular sieve and the Carbon-monoxide is introduced into the IRMS where its oxygen isotopic composition is measured.

It is well known in the art that determining ethanol $\delta^{13}C$ value can be done by means of the EA-IRMS (Elemental Analyzer-Isotope Ratio Mass Spectrometer), where the ethanol sample is first combusted in the presence of oxygen. Produced CO2 and water are then separated; $CO_2$ is purified and introduced into an IRMS where its carbon isotopic composition is measured.

According to another embodiment of the invention, the following four distinct isotopic values that can be used to identify the origin of alcohol-containing products are stored in a database: $\delta^{18}O$ and $\delta^{13}C$ values of an alcohol sample, $\delta D$ values of the olefin produced from the same alcohol sample, and $\delta^{18}O$ of water extracted from the product. Since determining the origin of sugar-containing products also includes adjusting isotope concentration to a pre-determined level prior to alcohol fermentation, the required isotope level should also be stored in the database.

Figure 11:
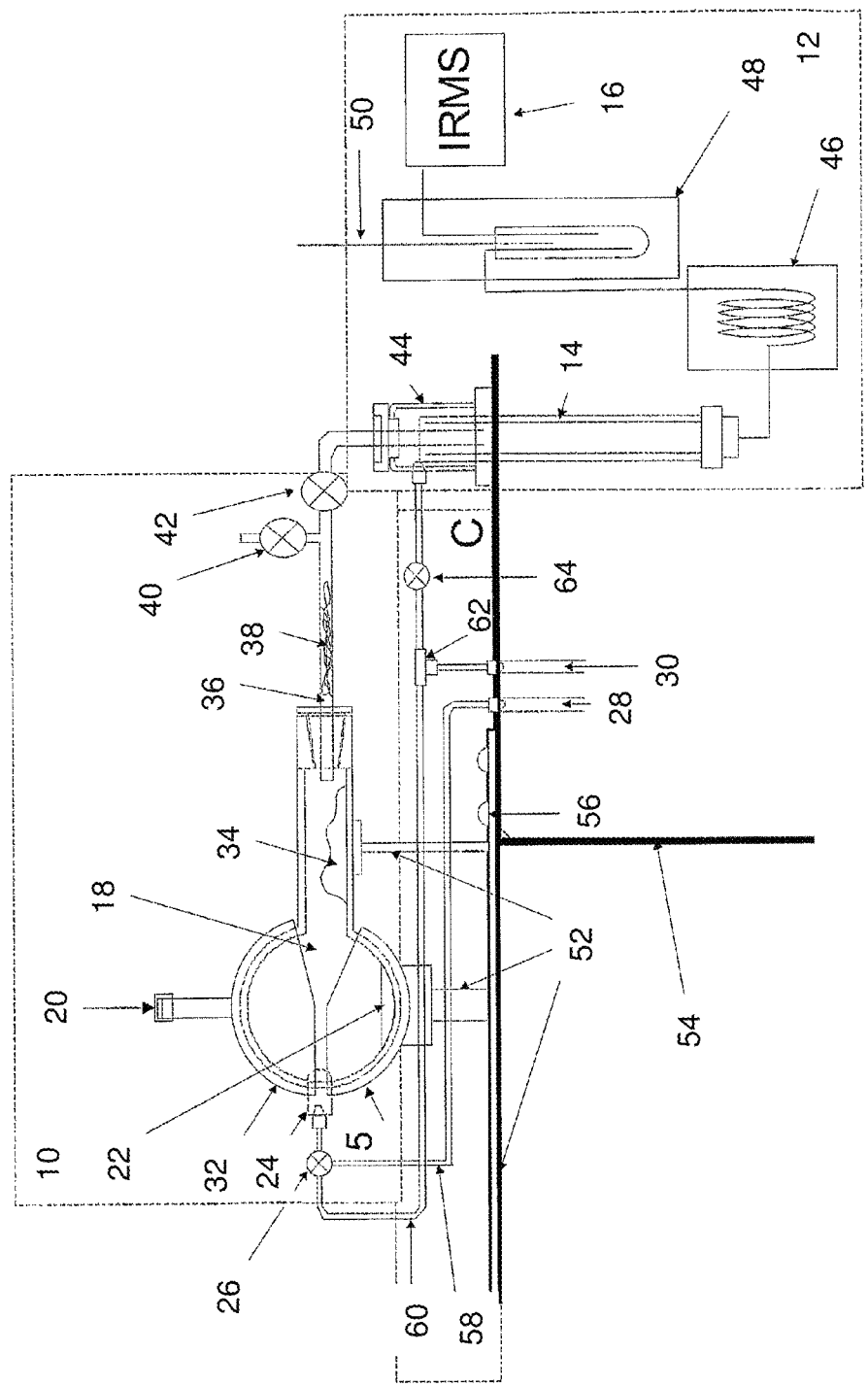
FIG. 11 shows an apparatus as configured in accordance with various embodiments of the invention.

In accordance with an embodiment shown in FIG. 11, an apparatus for determining origin of alcohol samples includes an alcohol dehydration chamber 10 and a detection module 12. In this embodiment, detection module 12 includes a pyrolysis reactor 14 and a continuous flow isotope spectrometer 16. Detection module 12 is connected to alcohol dehydration chamber 10 with a system of valves, connectors and capillary tubes for transfer of the analyzed sample and for the purging of alcohol dehydration chamber 10.

Alcohol dehydration chamber 10 includes a reaction vessel 18 with an upper opening having a stopper and septa 20, which is used for injection of an ethanol sample 22 by syringe, and a sideway opening 24 with a "switch" valve 26 for a helium "Reference" gas 28 and "Carrier" gas 30. Reaction vessel 18 is heated with a thermo-jacket 32, preferably comprising two electrical heaters. A part of reaction vessel 18 is preferably tube shaped, and may contain a dehydration catalyst 34. Dehydration catalyst 34 preferably comprises aluminum oxide (Al2O3), silica gel, zeolite, or the mixture of those substances or materials with similar properties. Reaction vessel 18 is connected to a tube with a gas tight stopper 36. Inside tube 36 a small amount of silica gel or similar inert hygroscopic material 38 can be placed. Tube 36 is connected to two valves 40 and 42. Tube 36 is connected via injection connector 44 to pyrolysis reactor 14, which is connected via a gas chromatography column 46 and Interface Open Split 48, which has a capillary for Helium dilution 50, to Isotope Ratio Mass Spectrometer IRMS 16. Alcohol thermal dehydration chamber 10 rests on a stand 52, which is fixed to the housing of peripheral 54, which in turn supports pyrolysis reactor 14 via screws 56. A capillary tube 58 is connected with the output of helium "Reference" gas 28, which is used for chamber purging, and with "switch" valve 26. The capillary tube 60 is, over a "T" connector 62, connected to the main flow output of helium "Carrier" gas 30, and to "switch" valve 26. The main flow output of the helium "Carrier" gas 30 is connected via "T" connector 62 and the capillary tubing to a security valve 64 and injection connector 44 on pyrolysis reactor 14.

Alcohol thermal dehydration chamber allows removal of exchangeable hydrogen (or deuterium) atoms from the hydroxyl group without isotopic fractionation, which does not cause substantial change in isotopic composition of the non-exchangeable hydrogen. Measured δD values are stable and generally do not deviate, since they correspond to concentrations of hydrogen and deuterium atoms that are strongly bonded to carbon atoms of the ethene (ethylene) gas.

A preferred procedure for using the apparatus for online determination of isotopic composition of non-exchangeable hydrogen and deuterium atoms in ethanol samples is as follows:

The first phase includes purging alcohol thermal dehydration chamber 10 with inert gas helium. Prior to purging valve 42 is closed and valve 40 is open. "Switch" valve 26 is set to position for "Reference" gas helium 58 to flow, which purges alcohol thermal dehydration chamber 10. The flow of "Reference" gas 28 is preferably between 20 ml/min. and 200 ml/min. After purging, which does not have to last more than 15 minutes, valve 40 is closed, valve 42 is open, and "switch" valve 26 is moved to position to allow flow of "Carrier" gas helium 60. The flow of "carrier" gas 30 is preferably between 70 ml/min. and 170 ml/min. Reaction vessel 10 is heated with thermo-jacket 32 to a temperature preferably between 250° C. and 500° C. Preferably not more than 1 ml of distillated and isolated alcohol (ethanol) sample 22 from analyzed wine, beer or alcoholic drink or similar is injected. Upon entering the reaction vessel, sample 22 is momentarily vaporized into overheated alcoholic fume which, in a stream of helium, passes over dehydration catalyst 34. After dehydration, separation of water and absorption by catalyst, the ethene (ethylene) gas, through capillary tube 36 and opened valve 42, enters pyrolysis reactor 14, where it is degraded to elemental gases ($H_2$ and CO). The gas chromatography column 46 separates the hydrogen gas, which is conducted over Interface and its Open Split 48 into IRMS 16.

Figure 12:
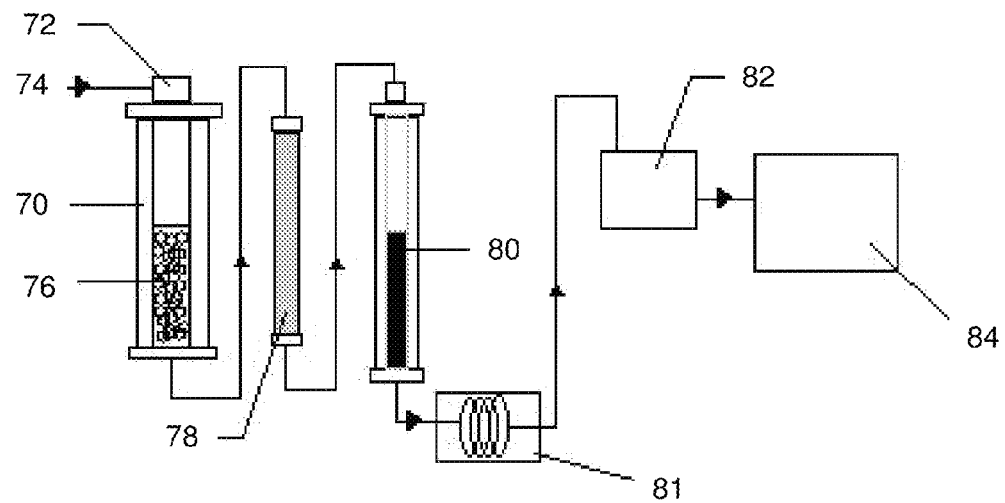
FIG. 12 shows an apparatus as configured in accordance with various embodiments of the invention.

FIG. 12 shows an embodiment with a continuous flow of helium. An alcohol sample is injected directly at the top of a dehydration column 70 through injection cap 72 with septa into helium streamed through inlet 74. Dehydration column 70, which is preferrably half-filled with solid dehydration catalyst granules 76, is heated to temperatures above 250° C. The injected alcohol sample evaporates at the entry of dehydration column 70 and overheated alcohol vapors are dehydrated over dehydration catalyst 76. The products of dehydration are olefin (alkene) and water, which are separated by removing the water in the column with hygroscopic material 78. Alkene is then further subjected to pyrolysis in a pyrolysis column 80, producing a gaseous mixture comprising elemental hydrogen gas. Pyrolysis column 80 is preferably filled with glassy carbon filling. The produced hydrogen gas is then separated from the gaseous mixture in a gas chromatography column 81 and conducted over interface with a capillary Open Split 82 and introduced into a Isotope Ratio Mass Spectrometer (IRMS) 84 for measuring its isotopic composition, i.e., isotopic relative ratio of hydrogen and deuterium in the hydrogen gas, and for calculating δD value of the measured isotopic composition.

Figure 13:
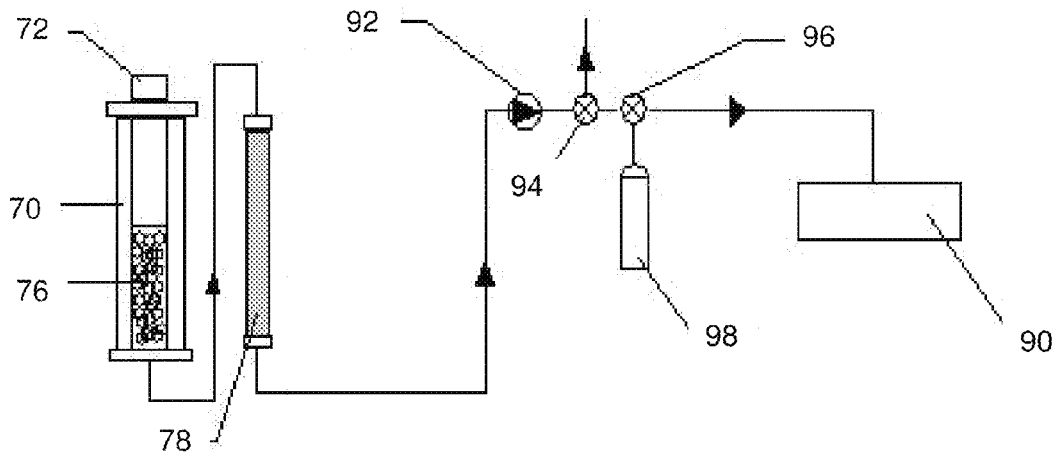
FIG. 13 shows an apparatus as configured in accordance with various embodiments of the invention.
Figure 14:
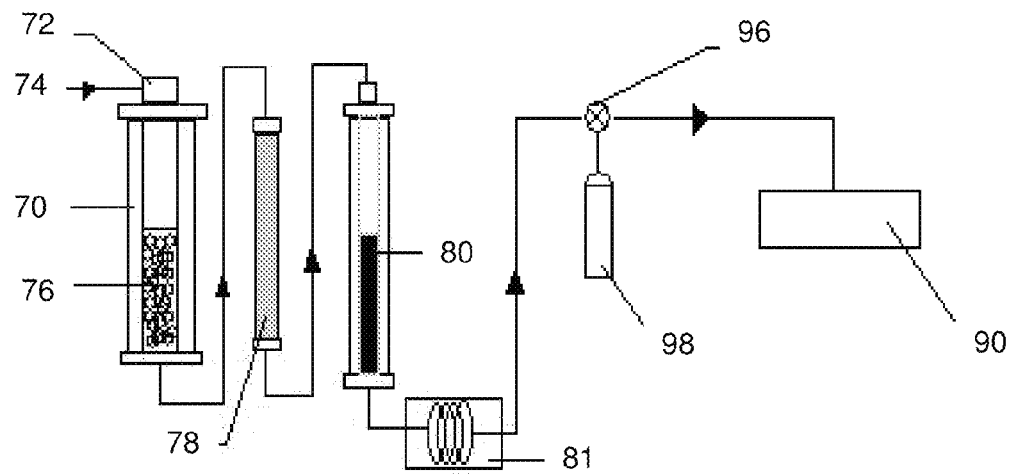
FIG. 14 shows an apparatus as configured in accordance with various embodiments of the invention.
Figure 15:
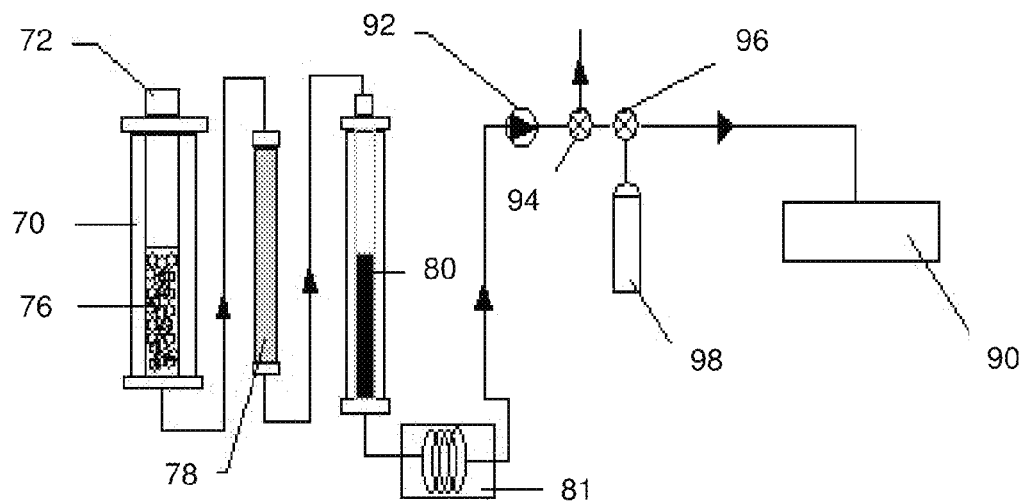
FIG. 15 shows an apparatus as configured in accordance with various embodiments of the invention.

According to embodiments shown in FIGS. 13-15, isotopic composition of non-exchangeable hydrogen and deuterium atoms in alcohol can also be determined using other techniques, such as a Wavelength Scanned-Cavity Ring-Down Spectroscopy (WS-CRDS).

The WS-CRDS method relies on the fact that nearly every small molecule (e.g., H2, H2O, N2O, CO2, C2H4) has a unique near-infrared absorption spectrum consisting of sharp, well resolved lines. However, conventional infrared spectrometers (and even those based on tunable laser diodes) do not have the requisite combination of spectral resolution, sensitivity, and large linear dynamic range necessary for measuring isotope ratios. WS-CRDS has all three attributes, and also has other advantages, such as speed, simplicity, long-term stability, and a small footprint. In WS-CRDS, light from a narrow-line width, wavelength tunable laser diode enters the sampling cavity which contains three exceptionally high reflectivity (>99.999%) minors. This cavity is automatically and precisely temperature and pressure stabilized. When the signal from the detector reaches a steady state condition, the laser is switched off. Because the minors do not have 100% reflectivity, the light intensity inside the cavity slowly leaks out and this ring-down (decay) is followed in real-time by a quantitative photo detector. If the cavity contains a gas species that even weakly absorbs light, this causes additional light loss. This, on the other hand, results in a shortened decay time, which forms the basis for a highly quantitative measurement.

Each of the sharp spectral absorption lines is due to the laser exciting vibrations and rotations in the target molecule. Because the frequency of these vibrations and rotations is dependent on the precise mass of the atoms, each isotopologue (e.g. H2O, HDO) has lines at different frequencies (i.e. wavelengths). Furthermore, WS-CRDS instruments have the spectral resolution and absolute wavelength precision necessary to isolate and uniquely measure these spectral lines. And because WS-CRDS delivers both ppt sensitivity and high dynamic range, even weaker lines corresponding to molecular species containing low abundance isotopes can be measured with high signal to noise ratio. So, by measuring the concentration of each of the individual isotopologues in this way, the instrument records the isotopic concentration ratio.

According to an embodiment shown in FIG. 13, ethylene gas is produced by alcohol dehydration, and its isotope composition, i.e., isotopic relative ratio of hydrogen and deuterium, along with δD value of the measured isotopic composition, is determined with a WS-CRDS isotope analyzer 90. An alcohol sample is injected directly at the top of a dehydration column 70 through injection cap 72 with septa. Dehydration column 70, which is preferably half-filled with solid dehydration catalyst granules 76, is heated to temperatures above 250° C. The injected alcohol sample evaporates at the entry of dehydration column 70, and overheated alcoholic vapors are dehydrated over dehydration catalyst 76. The products of dehydration, i.e., olefin (alkene) and water, are separated by removing the water in the column with hygroscopic material 78. Produced alkene is conducted to receiving tank 98 and from there to WS-CRDS isotope analyzer 90. According to this embodiment, instead of a helium carrier gas, a vacuum pump 92 provides internal atmosphere and driving force for the analyte to pass through the system to the receiving tank 98. The produced alkene gas is conducted through a 3-way valve 96 into receiving tank 98. Next, venting 3-way valve 94 is closed, separating receiving tank 98 from the source of the alkene gas. The alkene gas from tank 98 is then introduced over 3-way valve 96 into WS-CRDS isotope analyzer 90, for measuring isotopic composition, i.e., isotopic relative ratio of hydrogen and deuterium of the alkene gas, and for calculating δD value of the measured isotopic composition. Finally, venting 3-way valve 94 is used to release the gas from the system, and the entire process is repeated with another alcohol sample.

According to the embodiment shown in FIG. 14, an alcohol sample is introduced into a helium stream 74, and the mixture is dehydrated in dehydration column 70. Resulting ethylene and water are separated by removing water with hygroscopic material 78, and the ethylene gas is subjected to pyrolysis in column 80. Gas chromatography column 81 is used to extract hydrogen gas from a gaseous mixture produced by pyrolysis. The extracted hydrogen gas is conducted through 3-way valve 96 into receiving tank 98. Next, 3-way valve 96 is set to conduct the hydrogen gas from tank 98 into WS-CRDS isotope analyzer 90, for measuring isotopic composition, i.e., isotopic relative ratio of hydrogen and deuterium in the hydrogen gas, and for calculating $\delta D$ value of the measured isotopic composition.

As shown in FIG. 15, in absence of a helium carrier gas, a vacuum pump 92 can be used to provide internal atmosphere and driving force for analyte to travel trough the system to tank 98. Dehydration column 70 is preferrably half-filled with solid dehydration catalyst granules 76 and heated to temperatures above 250° C. The injected alcohol sample evaporates at the entry of dehydration column 70 and overheated alcohol vapors are dehydrated over dehydration catalyst 76. The products of dehydration are olefin (alkene) and water, which are separated by removing the water in column with hygroscopic material 78. Alkene is then further subjected to pyrolysis in a pyrolysis column 80, producing a gaseous mixture comprising elemental hydrogen gas. Pyrolysis column 80 is preferably filled with glassy carbon filling. The produced hydrogen gas is then separated from the gaseous mixture in a gas chromatography column 81.

The produced hydrogen gas is conducted through 3-way valve 96 into receiving tank 98. Next, venting 3-way valve 94 is closed, separating receiving tank 98 from the source of the hydrogen gas. The hydrogen gas from tank 98 is then introduced over 3-way valve 96 into WS-CRDS isotope analyzer 90, for measuring isotopic composition, i.e., isotopic relative ratio of hydrogen and deuterium of the hydrogen gas, and for calculating $\delta D$ value of the measured isotopic composition. Finally, venting 3-way valve 94 is used to release the gas from the system, and the entire process is repeated with another alcohol sample.

Figure 16:
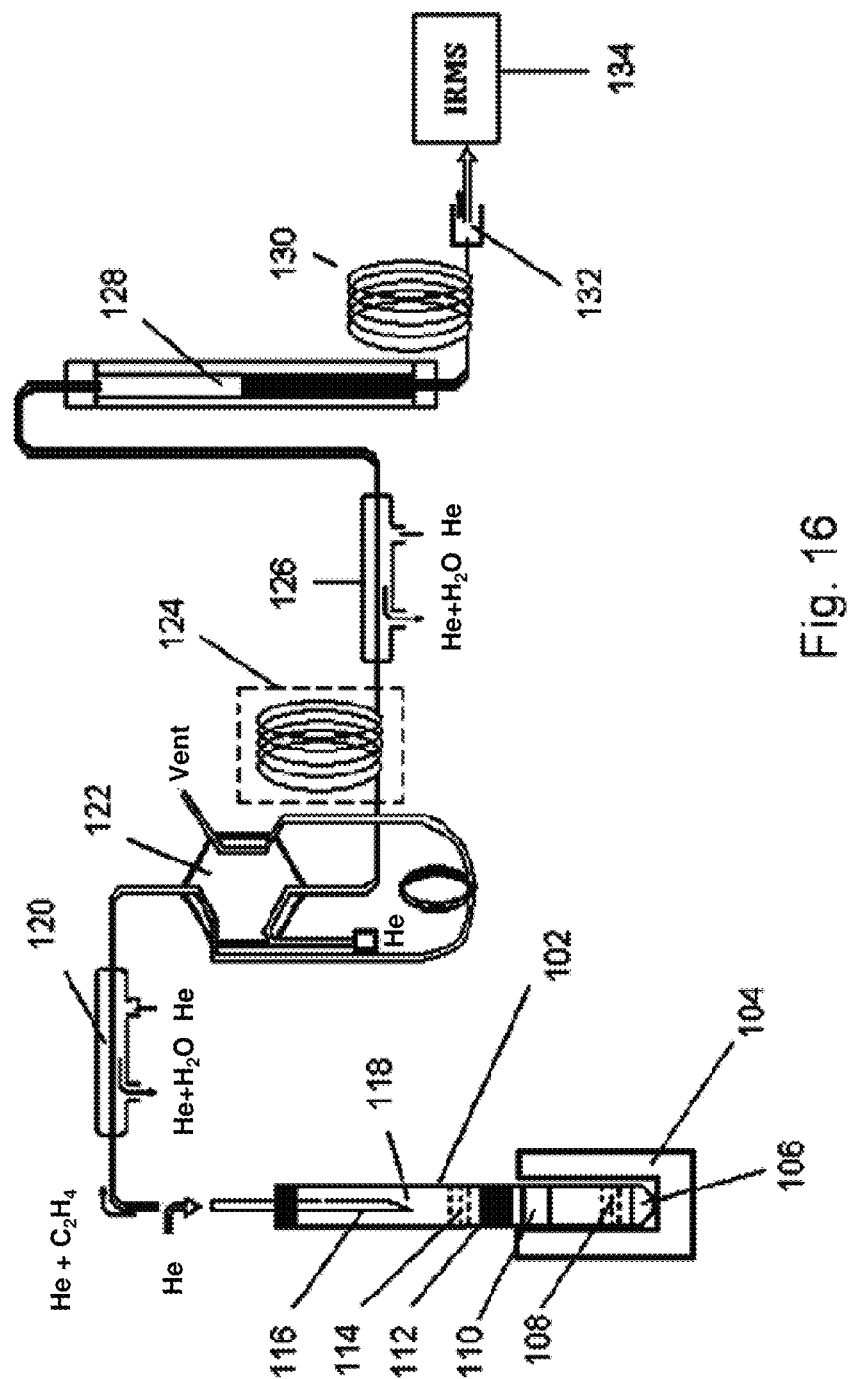
FIG. 16 shows an apparatus as configured in accordance with various embodiments of the invention.

As shown in FIG. 16, an embodiment includes injecting an alcohol sample trough a sideway capillary 102 to the bottom of a vacuumed vial 118. Vial 118 is heated by means of a thermo-jacket 104 to temperature over 350° C. An alcohol sample 106 evaporates and overheated alcohol vapors penetrate a one-way gas diaphragm 108. The alcohol vapors pass trough $Al_2O_3$ filling 110 where a dehydration reaction takes place. The resulted alkene gas is purified and separated from water vapors by passing through a hygroscopic material filling 112 and through a one-way diaphragm 114. The purified alkene gas enters vial 118. Injection needle 116 with sideway opening and double walls is used for injecting helium gas through the main stream and taking the ethylene in helium stream through sideway opening. Ethylene sample in helium stream is passed through first water removal 120 and enters Valco 6-port valve 122 where aliquot of the sample is kept in the loop. Next, by turning Valco valve 122 into second position, ethylene is passed through a gas chromatography column 124, which can be used for additional purification of the sample, and then through a second water removal 126. The ethylene sample then enters a pyrolysis reactor 128. The hydrogen gas formed during the pyrolysis is further purified and separated from the gaseous mixture in second gas chromatography column 130, and over an Interface with Active Open Split 132 passed into an Isotope Ratio Mass Spectrometer (IRMS) 134.

Another embodiment utilizes ethanol (alcohol) isotopicaly driven chemical dehydrogenation over solid catalyst surface to produce acetaldehyde (ethoxide) and hydrogen which stays bonded to catalyst active sites. This is a one step reaction without intermediate and very selective to acetaldehyde. This reaction generally requires temperatures between 200 and 300° C. Obtained acetaldehyde is then pyrolysed into elemental hydrogen and carbon monoxide gases which are further separated over a molecular sieve (GC Column). Separated hydrogen gas is then introduced into IRMS for measuring D/H ratio of the hydrogen gas. Other embodiments may include measuring D/H ratio in prepared acetaldehyde sample by means of Cavity Ring-Down Spectrometry (CRDS) analyzer.

Figure 17:
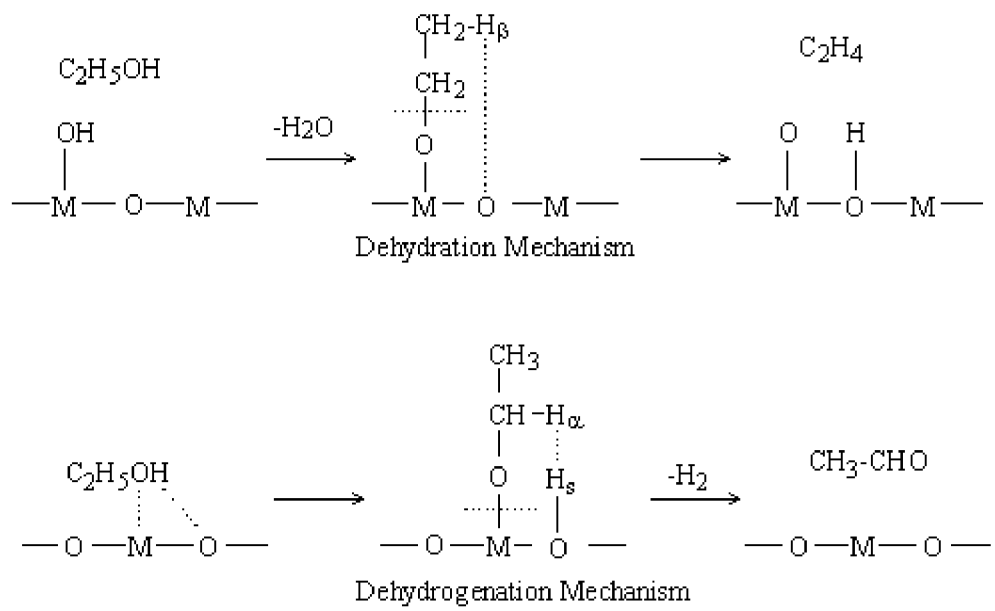
FIG. 17 shows a mechanism of ethanol dehydration and dehydrogenation in the presence of metal oxides.
Figure 18:
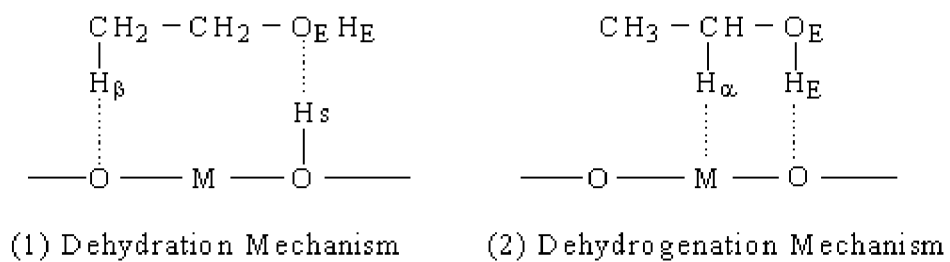
FIG. 18 shows a mechanism of ethanol dehydration and dehydrogenation in the presence of metal oxides.

FIGS. 17 and 18 show ethanol dehydration and dehydrogenation using oxides, where a metal atom is represented with the letter "M." The dehydrogenation reactions are isotopicaly driven with KIE (Kinetic Isotope Effect) which means that hydrogen atoms bonded on the methylene site of ethanol will more easily enter into a chemical reaction then deuterium atoms bonded to the same site ($—CH_2—$). The embodiments utilizing this method are similar to those based on ethanol dehydration, the differences include the temperature required for dehydrogenation and the catalyst selection. More specifically, the dehydrogenation reaction catalysts are selected from more basic metal oxides such as MgO, MnO, SnO, CdO, and $Mn_3O_5$. The dehydrogenation reaction generally produces hydrogen gas, aldehydes and/or ketones. The hydrogen gas is removed, and the aldehydes and/or ketones isotopic composition of hydrogen is measured. In one embodiment, produced aldehydes and/or ketones are subjected to pyrolysis, and the isotopic composition of the resulted hydrogen is measured and $\delta D$ is calculated. According to this embodiment, instruments such as IRMS and Wavelength Scanned-Cavity Ring-Down Spectrometry (WS-CRDS) analyzer can be used for measuring the hydrogen isotopic composition. In yet another embodiment, the hydrogen isotopic composition of the produced aldehydes and/or ketones is directly measured with WS-CRDS.

This invention does not require that all the advantageous features and all the advantages need to be incorporated into every embodiment of the invention.

Although the present invention has been described in considerable detail with reference to certain preferred versions thereof, other versions are possible, and the spirit and scope of the appended claims should not be limited to the description of the preferred versions contained herein.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

I claim:

1. A process for determining origin of a food product containing alcohols or sugars, comprising:
   preparing an alcohol sample from the food product;
   at least partly converting the alcohol sample into an olefin by dehydration wherein exchangeable hydrogen atoms and exchangeable deuterium atoms in the alcohol sample are removed;

measuring a relative ratio of hydrogen and deuterium of the olefin, where the relative ratio of hydrogen and deuterium of the olefin represents a relative ratio of non-exchangeable hydrogen atoms and non-exchangeable deuterium atoms of the alcohol sample; and comparing the relative ratio of hydrogen and deuterium of the olefin with one or more known relative ratios of non-exchangeable hydrogen and non-exchangeable deuterium of olefins from food products with known origins.

2. The process of claim 1, wherein preparing the alcohol sample from the food product comprises:
preparing a food product sample from the food product;
fermenting the food product sample; and
isolating the alcohol sample from the fermented food product sample.

3. The process of claim 2, wherein preparing the food product sample from the food product comprises extracting a sugar sample from the food product, and wherein the food product sample comprises the extracted sugar.

4. The process of claim 1, wherein the dehydrating of the alcohol sample comprises using a dehydration catalyst to dehydrate the alcohol sample.

5. The process of claim 4, wherein the dehydration catalyst is selected from a group consisting of: $Al_2O_3$, silica gel, and zeolite.

6. The process of claim 1, wherein the measuring comprises:
at least partly degrading the olefin into a gaseous mixture comprising a hydrogen gas; and
measuring a relative ratio of hydrogen and deuterium of the hydrogen gas where the relative ratio of hydrogen and deuterium of the hydrogen gas represents a relative ratio of non-exchangeable hydrogen atoms and non-exchangeable deuterium atoms of the alcohol sample, and where the relative ratio of hydrogen and deuterium of the olefin is the relative ratio of hydrogen and deuterium of the hydrogen gas.

7. The process of claim 6, wherein the at least partially degrading the olefin into the gaseous mixture comprises the hydrogen gas, comprises pyrolysis of the olefin.

8. The process of claim 6, wherein the measuring the relative ratio of hydrogen and deuterium of the hydrogen gas, is further defined in that an Isotope Ratio Mass Spectrometer is used to perform the measuring.

9. The process of claim 6, wherein the measuring the relative ratio of hydrogen and deuterium of the hydrogen gas, is further defined in that a Cavity Ring-Down Spectroscopy Analyzer is used to perform the measuring.

10. The process of claim 1, wherein the measuring is further defined in that a Cavity Ring-Down Spectroscopy Analyzer is used to perform the measuring.

11. The process of claim 1, wherein the comparing comprises:
calculating a δD value based on the relative ratio of hydrogen and deuterium of the olefin; and
comparing the calculated δD value with δD values of the food products having known origins.

12. The process of claim 1, wherein the preparing is further defined in that the food product is selected from a group consisting of wine, alcoholic beverages, fermented fruit juices, diluted and fermented honey, food products containing ethanol, and food products containing fermentable sugars.

13. The process of claim 1, further comprising:
measuring an isotopic relative
ratio selected from a group consisting of
an isotopic relative ratio of oxygen in water molecules of the food product,
an isotopic relative ratio of carbon in alcohol molecules of the food product, and
an isotopic relative ratio of oxygen in alcohol molecules of the food product; and,
comparing the isotopic relative ratio with a one or more respective known isotopic relative ratios from the food products with known origins.

14. A process of measuring a relative ratio of isotopes in an alcohol-containing composition of matter to determine an origin of the alcohol-containing composition of matter, comprising:
purging an alcohol thermal dehydration vessel;
heating the dehydration vessel;
injecting a preliminary isolated alcohol sample;
vaporizing the alcohol sample into overheated alcoholic fume which passes over dehydration catalyst to remove exchangeable hydrogen and exchangeable deuterium from the alcohol sample resulting in an alkene gas;
passing the alkene gas into a pyrolysis reactor and over gas chromatography column to an interface so the alkene gas is detected on an isotope ratio mass spectrometer;
measuring a hydrogen and deuterium relative ratio of alkene gas molecules of the alkene gas, where the hydrogen and deuterium relative ratio represents a relative ratio of non-exchangeable hydrogen atoms and non-exchangeable deuterium atoms of the alcohol sample; and,
comparing the relative ratio of hydrogen and deuterium of the alkene with one or more known relative ratios of non-exchangeable hydrogen and non-exchangeable deuterium of alkene from food products with known origins.

15. The process of claim 14, further comprising comparing the measured hydrogen and deuterium relative ratio with a relative ratio of hydrogen and deuterium in alkene molecules obtained from an alcohol-containing composition of matter of known origin.

16. The process of claim 14, wherein the injecting the preliminary isolated alcohol sample is further defined in that the isolated alcohol sample was obtained from the alcohol-containing composition of matter selected from a group consisting of: wine, alcoholic beverages, fermented fruit juices, diluted and fermented honey, food products containing ethanol, and food products containing fermentable sugars.

17. The process of claim 14, further comprising extracting a hydrogen gas by separating hydrogen atoms from the alkene gas molecules.

18. The process of claim 17, wherein the separating hydrogen atoms from the alkene gas molecules comprises pyrolysis of the alkene gas molecules and separating the hydrogen gas from the gaseous mixture.

19. A method of determining origin of a food product containing ethanol, comprising:
preparing an ethanol sample from the food product;
at least partly converting the ethanol sample into ethylene by dehydrating the ethanol sample so that exchangeable hydrogen and exchangeable deuterium from the ethanol are removed;
measuring a relative ratio of hydrogen and deuterium of the ethylene, where the relative ratio of hydrogen and deuterium of the ethylene represents a relative ratio of non-exchangeable hydrogen atoms and non-exchangeable deuterium atoms of the ethanol sample; and comparing the measured relative ratio of hydrogen and deuterium of the ethylene with known relative ratios of non-exchangeable hydrogen and non-exchangeable deuterium of ethylene from food products with known origins.

20. The process of claim 1, wherein the at least partly converting the alcohol sample into an olefin by dehydration comprises causing an E2 elimination reaction resulting in the formation of the olefin and water in one step.

21. The process of claim 1, wherein the at least partly converting the alcohol sample into an olefin by dehydration comprises heating the alcohol sample to between 250 degrees Celsius to 500 degrees Celsius.

22. The process of claim 1, wherein the measuring is further defined in that an Isotope Ratio Mass Spectrometer is used to perform the measuring.

23. The process of claim 1, further comprising:
measuring an isotopic relative ratio of oxygen in water molecules of the food product;
measuring an isotopic relative ratio of carbon in alcohol molecules of the food product;
measuring an isotopic relative ratio of oxygen in alcohol molecules of the food product; and,
comparing a measured food product signature of the food product comprising
the isotopic relative ratio of oxygen in water molecules of the food product, the isotopic relative ratio of carbon in alcohol molecules of the food product, the isotopic relative ratio of oxygen in alcohol molecules of the food product, and the relative ratio of hydrogen and deuterium of the olefin,
with one or more know food product signatures from food products of known origins, each one or more of the known food product signatures comprising
a known isotopic relative ratio of oxygen in water molecules of the corresponding food product of known origin, a known isotopic relative ratio of carbon in alcohol molecules of the corresponding food product of known origin, a known isotopic relative ratio of oxygen in alcohol molecules of the corresponding food product of known origin, and a known relative ratios of non-exchangeable hydrogen and non-exchangeable deuterium of olefins of the corresponding food product of known origin.

\* \* \* \* \*